April 17, 1956 R. L. BYRUM Plant Pat. 1,468
ROSE PLANT
Filed June 1, 1955
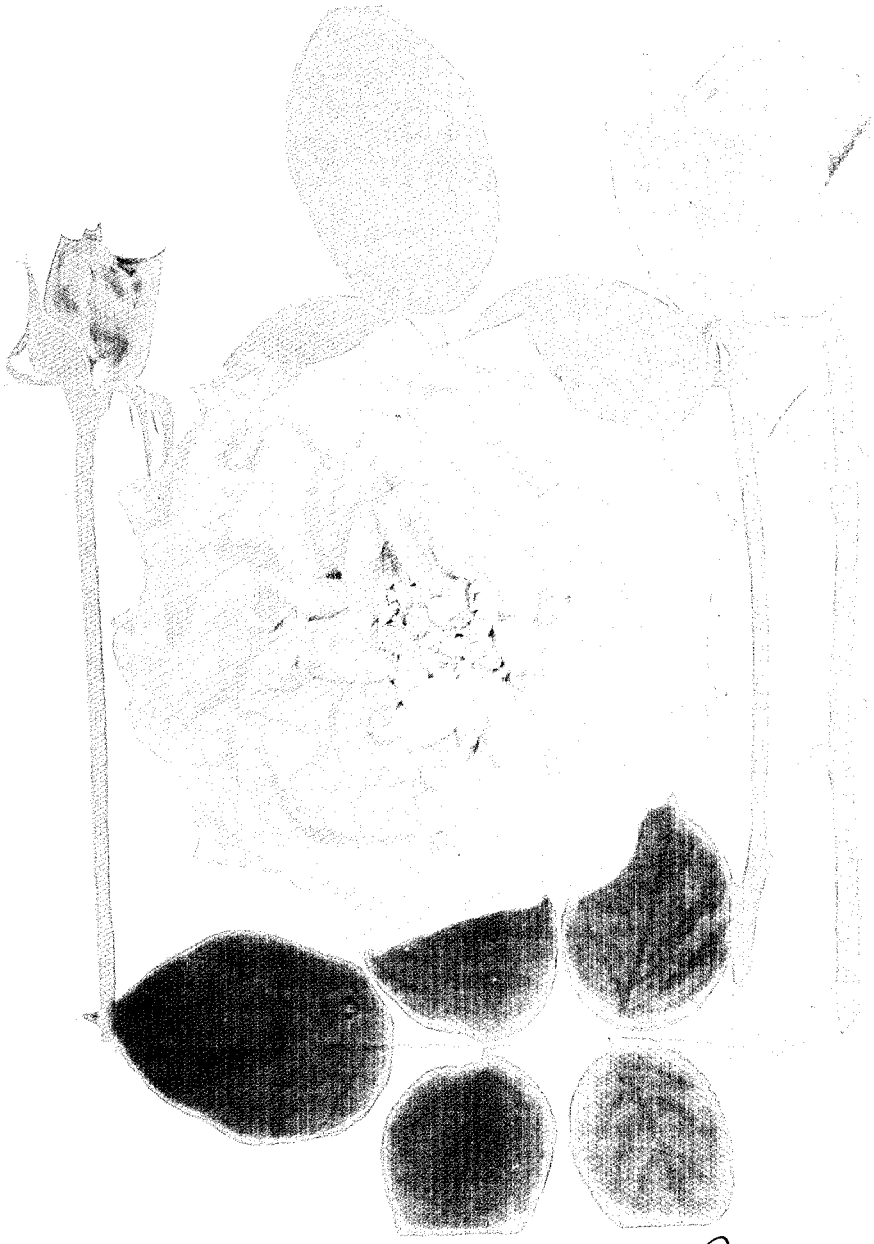
Inventor.
R. L. Byrum
By: Robb & Robb
Attorneys.

United States Patent Office

Plant Pat. 1,468
Patented Apr. 17, 1956

1,468

ROSE PLANT

Roy L. Byrum, Richmond, Ind., assignor to Joseph H. Hill Company, Richmond, Ind., a corporation of Indiana Application June 1, 1955, Serial No. 512,594

1 Claim. (Cl. 47—61)

The present invention relates to a new and distinct variety of rose plant of the hybrid tea class, which was originated by me by crossing the variety "Happiness" (Plant Patent No. 911) with the variety "Sister Kenny" (Plant Patent No. 1,146).

The primary objective in making this cross was to improve the growth, flower production and flower color characteristics of the variety "Happiness." This objective was fully achieved as evidenced by the following.

In comparison with the pollen parent, "Happiness," my new variety is a better winter forcer; holds its bud and bloom size in extremely hot weather; is more productive and freer in growth; the blooms keep longer and do not open as fast, and the color of the blooms is more brilliant and is not so dark in winter. Otherwise, the new variety is generally similar to this pollen parent.

As compared with its seed parent, "Sister Kenny," the new variety is a hybrid tea, whereas the seed parent is a polyantha, and this parent variety is too single for commercially acceptable use for greenhouse cut-flower forcing.

In addition to being a good winter forcer, my new variety is also a good summer rose, and the distinctive and brilliant color of its flowers also make it a commercially useful and desirable variety.

The foregoing characteristics and distinctions definitely differentiate the new variety from its parents, as well as from all other varieties of which I am aware, and asexual reproduction of the new variety by grafting, as performed at Richmond, Indiana, as well as by budding, as performed at Wills Point, Texas, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway"), Robert F. Wilson's Horticultural Colour Chart (hereinafter abbreviated at "Wilson") and Koster's Color Guide (hereinafter abbreviated as "Koster"), as indicated:

Type: Greenhouse; bush; seedling.
Class: Hybrid tea.
Breeding: Seedling.
*Seed parent.*—"Sister Kenny."
*Pollen parent.*—"Happiness."
Propagation: Holds its distinguishing characteristics through succeeding propagations by both grafting and budding.

FLOWER

Locality where grown and observed: Richmond, Indiana.
Flowers borne: Singly to stem; on very long, strong stems.

Quantity of bloom: Free, in greenhouse.
Continuity: Continuous.
Fragrance: Slight. Nature—tea.
Bud:
*Peduncle.* — Medium length; medium diameter; strong; erect. Bark—smooth. Color — Spinach Green, Plate 0960/1 (Wilson). Thorns — few. Color — Pod Green, Plate 061/2 (Wilson). Prickles—numerous. Color—Pod Green, Plate 061/2 (Wilson). Hairs—none.
*Before calyx breaks.*—Size—medium large. Form —long-pointed; ovoid; with a conspicuous neck; with foliaceous appendages on the surface of the bud; with stout, much-cut foliaceous parts extending beyond the tip of the bud equal to ¾ or more of its length. Color—Spinach Green, Plate 0960/2 (Wilson).
*As calyx breaks.* — Color (outside of petal) — Chrysanthemum Crimson, Plate 824/1 (Wilson), overlaid with Indian Lake, Plate 826 (Wilson).
*As first petal opens.*—Size—medium large. Form — long-pointed; ovoid. Color: Outside — Rose Red, Plate 724 (Wilson); Inside — Rose Red, Plate 724 (Wilson), overlaid with a dark velvety Red which has no match in color charts.
*Opening.*—Opens up well in greenhouse; is normally affected by weather conditions, but has no unusual characteristics.
Bloom:
*Size (when fully open).* — Very large; from 4½ inches to 5½ inches.
*Petalage.* — Double (more petals, but the stamens are not hidden); from 45 to 50 petals; arranged irregularly.
*Form.*—Full and high-centered at first, becoming open and high-centered; petals being at first tightly rolled outward, but later becoming loosely rolled outward at maturity.
Petals: Moderately thick. Inside—velvety. Outside—satiny.
*Shape.*—Outside petals—obovate; apex obtuse. Intermediate petals—obovate; apex obtuse. Inside petals—obovate; apex obtuse.

This description of a newly opened flower was made from a rose grown in a greenhouse in the month of November, at Richmond, Indiana:

Color:
*Outside petal.* — Outside surface—Rose Red, Plate 724/3 (Wilson), very lightly overlaid with shades of Rose Red, Plate 724/1 (Wilson). Inside surface—Rose Red, Plate 724/1 (Wilson), overlaid with a velvety Red which is very near Rose Red, Plate 724 (Wilson).
*Intermediate petal.* — Outside surface—Rose Red, Plate 724/2 (Wilson). Inside surface — Rose Red, Plate 724 (Wilson).
*Inner petal.* — Outside surface—Rose Red, Plate 724/2 (Wilson). Inside surface — Rose Red, Plate 724 (Wilson).

This description was made from a rose that was open for 3 days in a greenhouse in the month of November, at Richmond, Indiana:

Color:
*Outside petal.*—Outside surface—Rose Red, Plate 724/3 (Wilson). Inside surface—Rose Red, Plate 724/2 (Wilson).
*Intermediate petal.*—Outside surface—Rose Red, Plate 724/2 (Wilson). Inside surface—Rose Red, Plate 724/2 (Wilson).
*Inner petal.*—Oustide surface—Rose Red, Plate 724/2 (Wilson). Inside surface—Rose Red, Plate 724/2 (Wilson), with a few having white stripes extending lengthwise through center.

General color effect:

*Newly opened flower.*—Rose Red, Plate 724 (Wilson). 3-days open.—Rose Red, Plate 724/2 (Wilson).

Behavior: Persist; normally affected by weather, but without unusual characteristics; fading to Rose Red Plate 724/3 (Wilson).

Flower longevity: Cut roses grown in greenhouse and kept at living-room temperatures—4 or 5 days in November.

PLANT

Foliage:

*Leaves.*—Compound of 3 to 5 leaflets; abundant; medium large size; moderately heavy; wrinkled.

*Leaflets.*—Shape—ovoid. Apex—mucronate. Base—round. Margin—simply serrate.

*Color.*—Mature: upper surface—Near Spinach Green, Plate 0960 (Wilson), but slightly darker; under surface—Sage Green, Plate XLVII (Ridgway). Young: upper surface—Pod Green, Plate 061 (Wilson), shading through Pod Green, Plate 061/1 (Wilson) to Pod Green, Plate 061/2 (Wilson); under surface—Pod Green, Plate 061 (Wilson), shading through Pod Green, Plate 061/1 (Wilson) to Pod Green, Plate 061/2 (Wilson).

*Rachis (the supporting stem of the compound leaf.*—Medium heavy. Upper side—grooved. Under side—prickly.

*Stipules.*—Moderately short; moderately narrow; with very short points turning out at an angle of less than 45°.

Growth:

*Habit.*—Bush; upright; branched.

*Growth.*—Vigorous.

*Canes.*—Large diameter.

*Main stems.*—Color—Sage Green, Plate 78 (Koster), overlaid or blotched with Tobacco Brown, Plate 88 (Koster). Thorns—many; medium length; hooked downward; with long base. Color.—Fawn, Plate 89 (Koster). Prickles—several. Color—Fawn, Plate 89 (Koster). Hairs—None.

*Branches.*—Color—Spinach Green, Plate 0960/1 (Wilson). Thorns—several; medium length; hooked downward. Color—Grape Green, Plate XLI (Ridgway) at tip, changing to Purplish Mauve, Plate 53 (Koster) at base. Prickles—few. Color—Grape Green, Plate XLI (Ridgway). Hairs—none.

*New shoots.*—Color—Pod Green, Plate 061/1 (Wilson). Thorns—several; medium length; hooked downward; with long base. Color—Corinthian Red, Plate XXVII (Ridgway). Prickles—few. Color—Corinthian Red, Plate XXVII (Ridgway). Hairs—none.

REPRODUCTIVE ORGANS

Stamens: Many; arranged regularly about pistils.

Filaments: Long; most with anthers. Color—Tyrian Rose, Plate 24/2 (Wilson).

Anthers: Medium large; all open at once. Color—Yellow Ochre, Plate 07/2 (Wilson).

Pollen: Abundant. Color—Maize Yellow, Plate 607/1 (Wilson).

Pistils: Many.

Styles: Uneven; medium length; moderately thin; bunched. Color—Rose Pink, Plate 427/2 (Wilson).

Stigma: Color—Pure White, Plate 1 (Koster).

Ovularies: All encased in calyx.

Sepals: Permanent; long; spear-shaped. Color: Inside—Spinach Green, Plate 75 (Koster), overlaid with white fuzz; outside—Spinach Green, Plate 75 (Koster).

I claim:

A new and distinct variety of rose plant of the hydrid tea class, substantially as herein shown and described, characterized particularly as to novelty by its improved flower productivity, habits of growth, flower color and winter forcing qualities as compared with its pollen parent variety "Happiness" (Plant Patent No. 911).

No references cited.